United States Patent
Mark et al.

(10) Patent No.: US 7,556,622 B2
(45) Date of Patent: Jul. 7, 2009

(54) SELECTIVELY OPENABLE TISSUE FILTER

(75) Inventors: Joseph L. Mark, Indianapolis, IN (US); Zachary R. Nicoson, Indianapolis, IN (US); Terry D. Hardin, Indianapolis, IN (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 325 days.

(21) Appl. No.: 11/132,034

(22) Filed: May 18, 2005

(65) Prior Publication Data
US 2006/0260994 A1 Nov. 23, 2006

(51) Int. Cl.
*A61M 1/00* (2006.01)
*A61B 10/02* (2006.01)

(52) U.S. Cl. .............. 604/319; 600/565; 600/566; 210/348

(58) Field of Classification Search ........... 604/319; 600/565–567
See application file for complete search history.

(56) References Cited

U.S. PATENT DOCUMENTS

| | | | | |
|---|---|---|---|---|
| 1,337,733 | A | * | 4/1920 | Sweetland et al. ........... 220/848 |
| 1,693,741 | A | * | 12/1928 | Wuest ........................ 210/448 |
| 1,734,652 | A | * | 11/1929 | Sweetland .................. 210/331 |
| 1,941,982 | A | * | 1/1934 | Gill ............................ 210/282 |
| 2,047,714 | A | * | 7/1936 | Smith ..................... 285/148.14 |
| 2,656,930 | A | * | 10/1953 | De Vries .................... 210/232 |
| 2,689,048 | A | * | 9/1954 | Powers ...................... 210/457 |
| 3,401,684 | A | | 9/1968 | Dremann |
| 3,456,806 | A | | 7/1969 | Borston |
| 3,561,429 | A | | 2/1971 | Jewett et al. |
| 3,785,380 | A | * | 1/1974 | Brumfield .................. 604/119 |
| 3,815,604 | A | | 6/1974 | O'Malley et al. |
| 3,833,000 | A | | 9/1974 | Bridgman |
| 3,889,657 | A | | 6/1975 | Baumgarten |
| 3,890,712 | A | | 6/1975 | Lopez |
| 3,937,222 | A | | 2/1976 | Banko |
| 3,938,505 | A | | 2/1976 | Jamshidi |
| 3,945,375 | A | | 3/1976 | Banko |
| 3,994,297 | A | | 11/1976 | Kopf |
| 4,007,742 | A | | 2/1977 | Banko |

(Continued)

FOREIGN PATENT DOCUMENTS

DE 9112550 11/1991

(Continued)

OTHER PUBLICATIONS

WebMd Medical Dictionary "What is tissue?" 2006, http://dictionary.webmd.com/terms/tissue.xml.*

(Continued)

*Primary Examiner*—Tatyana Zalukaeva
*Assistant Examiner*—Paula L Craig
(74) *Attorney, Agent, or Firm*—Rader, Fishman & Grauer, PLLC (57) ABSTRACT

A tissue filter for medical collection is disclosed. The tissue filter includes a first member, a second member, and filter material secured thereto. The first and second members are selectively engaged with one another to define a filter body having a collection cavity. The collection cavity is open at one end for tissue to flow into the collection cavity. The first member and the second member may be selectively separated to facilitate tissue removal from the collection cavity.

9 Claims, 6 Drawing Sheets

U.S. PATENT DOCUMENTS

| | | | |
|---|---|---|---|
| D243,559 S | 3/1977 | Hoyle et al. | |
| 4,019,514 A | 4/1977 | Banko | |
| 4,083,706 A | 4/1978 | Wiley | |
| 4,101,756 A | 7/1978 | Yamano | |
| 4,117,843 A | 10/1978 | Banko | |
| 4,159,773 A | 7/1979 | Losenno | |
| 4,167,943 A | 9/1979 | Banko | |
| 4,167,944 A | 9/1979 | Banko | |
| 4,177,814 A | 12/1979 | Knepshield et al. | |
| 4,210,146 A | 7/1980 | Banko | |
| 4,220,252 A * | 9/1980 | Beall et al. | 422/102 |
| 4,221,225 A | 9/1980 | Sloan et al. | |
| 4,257,425 A | 3/1981 | Ryan | |
| 4,282,098 A * | 8/1981 | Morgan, Jr. | 210/238 |
| 4,308,878 A | 1/1982 | Silva | |
| 4,316,465 A | 2/1982 | Dotson, Jr. | |
| 4,354,093 A | 10/1982 | Zago | |
| 4,368,734 A | 1/1983 | Banko | |
| 4,382,808 A * | 5/1983 | Van Wormer et al. | 55/418 |
| 4,468,217 A * | 8/1984 | Kuzmick et al. | 604/48 |
| 4,513,745 A | 4/1985 | Amoils | |
| 4,530,356 A | 7/1985 | Helfgott et al. | |
| 4,533,818 A | 8/1985 | Green | |
| 4,549,554 A | 10/1985 | Markham | |
| 4,562,838 A | 1/1986 | Walker | |
| 4,644,951 A | 2/1987 | Bays | |
| 4,651,753 A | 3/1987 | Lifton | |
| 4,696,298 A | 9/1987 | Higgins et al. | |
| 4,708,147 A | 11/1987 | Haaga | |
| 4,803,341 A | 2/1989 | Barowski et al. | |
| 4,817,631 A | 4/1989 | Schnepp-Pesch et al. | |
| 4,850,373 A | 7/1989 | Zatloukal et al. | |
| 4,871,074 A | 10/1989 | Bryson et al. | |
| 4,886,492 A * | 12/1989 | Brooke | 604/541 |
| 4,893,635 A * | 1/1990 | de Groot et al. | 600/567 |
| 4,919,146 A | 4/1990 | Rhinehart et al. | |
| 4,926,877 A | 5/1990 | Bookwalter | |
| RE33,258 E | 7/1990 | Onik et al. | |
| 4,973,019 A | 11/1990 | Baird et al. | |
| 4,985,027 A | 1/1991 | Dressel | |
| 4,989,614 A * | 2/1991 | Dejter et al. | 600/565 |
| 5,027,827 A | 7/1991 | Cody et al. | |
| 5,031,778 A | 7/1991 | Edgecombe | |
| 5,054,615 A | 10/1991 | Stillwagon et al. | |
| 5,074,311 A | 12/1991 | Hasson | |
| 5,080,869 A * | 1/1992 | McCormick | 422/102 |
| 5,090,649 A | 2/1992 | Tipp | |
| 5,108,381 A * | 4/1992 | Kolozsi | 604/319 |
| 5,124,532 A | 6/1992 | Hafey et al. | |
| 5,141,189 A | 8/1992 | Andrew | |
| D329,304 S | 9/1992 | Tipp | |
| 5,172,701 A | 12/1992 | Leigh | |
| D332,670 S | 1/1993 | McFarland | |
| 5,183,052 A | 2/1993 | Terwilliger | |
| 5,192,439 A * | 3/1993 | Roth et al. | 210/485 |
| 5,197,968 A * | 3/1993 | Clement | 606/115 |
| 5,213,110 A | 5/1993 | Kedem et al. | |
| 5,243,994 A * | 9/1993 | Ranalletta | 600/567 |
| D342,585 S | 12/1993 | Fischbach et al. | |
| 5,275,609 A | 1/1994 | Pingleton et al. | |
| 5,284,156 A * | 2/1994 | Schramm et al. | 600/567 |
| 5,285,795 A | 2/1994 | Ryan et al. | |
| 5,295,980 A | 3/1994 | Ersek | |
| 5,348,022 A | 9/1994 | Leight et al. | |
| 5,358,638 A * | 10/1994 | Gershenson | 210/448 |
| 5,403,276 A | 4/1995 | Schechter et al. | |
| 5,411,513 A | 5/1995 | Ireland et al. | |
| 5,423,844 A | 6/1995 | Miller | |
| 5,429,138 A | 7/1995 | Jamshidi | |
| 5,456,267 A | 10/1995 | Stark | |
| 5,458,112 A | 10/1995 | Weaver | |
| 5,464,300 A | 11/1995 | Crainich | |
| 5,505,210 A | 4/1996 | Clement | |
| 5,520,635 A | 5/1996 | Gelbfish | |
| 5,520,801 A | 5/1996 | Gerber et al. | |
| D371,220 S | 6/1996 | Behrens | |
| 5,526,822 A | 6/1996 | Burbank et al. | |
| 5,533,642 A * | 7/1996 | Lafond et al. | 220/326 |
| 5,543,114 A * | 8/1996 | Dudek | 422/102 |
| 5,575,293 A | 11/1996 | Miller et al. | |
| 5,580,347 A | 12/1996 | Reimels | |
| D377,996 S | 2/1997 | Gilbert | |
| 5,615,782 A | 4/1997 | Choe | |
| D379,554 S | 5/1997 | Landers | |
| 5,630,939 A * | 5/1997 | Bulard et al. | 210/416.1 |
| 5,643,304 A | 7/1997 | Schechter et al. | |
| 5,649,547 A | 7/1997 | Ritchart et al. | |
| 5,669,876 A | 9/1997 | Schechter et al. | |
| 5,669,923 A | 9/1997 | Gordon | |
| D386,818 S | 11/1997 | Boomfield | |
| 5,685,840 A | 11/1997 | Schechter et al. | |
| 5,730,717 A | 3/1998 | Gelbfish | |
| 5,769,086 A | 6/1998 | Ritchart et al. | |
| 5,775,333 A | 7/1998 | Burbank et al. | |
| 5,779,649 A * | 7/1998 | Herbert | 600/571 |
| 5,782,849 A | 7/1998 | Miller | |
| 5,788,651 A | 8/1998 | Weilandt | |
| 5,794,626 A | 8/1998 | Kieturakis | |
| 5,794,799 A | 8/1998 | Collins et al. | |
| 5,810,806 A | 9/1998 | Ritchart et al. | |
| 5,843,111 A | 12/1998 | Vijfvinkel | |
| 5,848,978 A | 12/1998 | Cecchi | |
| D403,810 S | 1/1999 | Owens | |
| 5,893,862 A | 4/1999 | Pratt et al. | |
| 5,911,701 A | 6/1999 | Miller et al. | |
| 5,913,857 A | 6/1999 | Ritchart et al. | |
| 5,916,229 A | 6/1999 | Evans | |
| 5,928,164 A | 7/1999 | Burbank et al. | |
| 5,928,218 A | 7/1999 | Gelbfish | |
| 5,944,673 A | 8/1999 | Gregoire et al. | |
| 5,964,716 A | 10/1999 | Gregoire et al. | |
| 5,980,469 A | 11/1999 | Burbank et al. | |
| 5,980,546 A | 11/1999 | Hood | |
| 5,997,560 A | 12/1999 | Miller | |
| 6,007,497 A | 12/1999 | Huitema | |
| 6,017,316 A | 1/2000 | Ritchart et al. | |
| 6,019,733 A | 2/2000 | Farascioni | |
| 6,022,324 A | 2/2000 | Skinner | |
| D423,717 S | 4/2000 | Taylor | |
| 6,050,955 A | 4/2000 | Bryan et al. | |
| D426,025 S | 5/2000 | Holmes et al. | |
| 6,077,230 A | 6/2000 | Gregoire et al. | |
| 6,080,113 A | 6/2000 | Heneveld et al. | |
| 6,085,749 A | 7/2000 | Wardle et al. | |
| 6,086,544 A | 7/2000 | Hibner et al. | |
| 6,096,042 A | 8/2000 | Herbert | |
| 6,109,446 A | 8/2000 | Foote | |
| 6,120,462 A | 9/2000 | Hibner et al. | |
| 6,120,463 A | 9/2000 | Bauer | |
| 6,123,299 A | 9/2000 | Zach, Sr. | |
| 6,142,955 A | 11/2000 | Farascioni et al. | |
| 6,162,187 A | 12/2000 | Buzzard et al. | |
| 6,193,414 B1 | 2/2001 | Balzano | |
| 6,193,673 B1 | 2/2001 | Voila et al. | |
| 6,273,862 B1 | 8/2001 | Privitera et al. | |
| 6,293,957 B1 | 9/2001 | Peters et al. | |
| 6,331,165 B1 * | 12/2001 | Turturro et al. | 600/562 |
| 6,346,107 B1 | 2/2002 | Cucin | |
| 6,402,701 B1 | 6/2002 | Kaplan et al. | |
| 6,428,487 B1 | 8/2002 | Burdorff et al. | |
| 6,461,350 B1 | 10/2002 | Underwood et al. | |
| 6,468,225 B1 | 10/2002 | Lundgren | |
| 6,468,227 B2 | 10/2002 | Zimmon | |
| 6,471,700 B1 | 10/2002 | Burbank et al. | |

| | | | |
|---|---|---|---|
| 6,485,436 B1 | 11/2002 | Truckai et al. | |
| 6,592,508 B1 | 7/2003 | Ravins et al. | |
| 6,632,182 B1 | 10/2003 | Treat | |
| 6,752,768 B2 | 6/2004 | Burdorff et al. | |
| 6,951,611 B2* | 10/2005 | Dannenmaier et al. | 210/321.89 |
| 7,041,217 B1* | 5/2006 | Close et al. | 210/232 |
| 7,226,424 B2 | 6/2007 | Ritchart et al. | |
| 7,316,726 B2 | 1/2008 | Schwindt | |
| 2001/0014785 A1 | 8/2001 | Sussman et al. | |
| 2002/0082519 A1* | 6/2002 | Miller et al. | 600/566 |
| 2002/0120212 A1* | 8/2002 | Ritchart et al. | 600/567 |
| 2003/0018281 A1* | 1/2003 | Huitema | 600/567 |
| 2003/0073929 A1* | 4/2003 | Baltschun et al. | 600/567 |
| 2003/0087423 A1* | 5/2003 | Haywood et al. | 435/270 |
| 2004/0049128 A1 | 3/2004 | Miller et al. | |
| 2004/0222137 A1* | 11/2004 | Hashimoto | 210/169 |
| 2004/0222145 A1* | 11/2004 | Onoue et al. | 210/435 |
| 2005/0049521 A1* | 3/2005 | Miller et al. | 600/565 |
| 2005/0113715 A1* | 5/2005 | Schwindt et al. | 600/566 |
| 2006/0155210 A1 | 7/2006 | Beckman et al. | |

FOREIGN PATENT DOCUMENTS

| | | |
|---|---|---|
| EP | 0541970 | 5/1993 |
| WO | WO-0197702 | 12/2001 |

OTHER PUBLICATIONS

Blood: definition, usage and pronunciation, YourDictionary.com, http://www.yourdictionary.com/blood.*

Blood-definition from Biology-Online.org. Oct. 3, 2005, http://www.biology-online.org/dictionary/Blood.*

Eionet GEMET Thesaurus, "blood (tissue)", Oct. 17, 2007, http://www.eionet.europa.eu/gemet/concept?cp=935.*

Biology 20-Investigation "Blood Tissue", www.blackgold.ab.ca/microtest/Biology 20 Labs/blood_tissue.pdf.*

International Search Report No. PCT/US01/51235 dated Dec. 10, 2002.

Publication in Design News entitled "Probe reduces breast biopsy trauma" by Joseph Ogando dated Aug. 7, 2000.

Steven K. Wagner, "Imaging News," Breast ultrasound spurs biopsy technology race, (Mar. 6, 1996).

International Search Report No. PCT/IB2008/051585 dated Aug. 30, 2006.

Office Action for U.S. Appl. No. 10/958,026 dated Jan. 10, 2005 (9 pages).

Amendment to Office Action for U.S. Appl. No. 10/958,026 dated Jan. 10, 2005. (7 pages).

Notice of Non-Compliant Amendment for U.S. Appl. No. 10/958,206 dated Apr. 20, 2005 (2 pages).

Response to Non-Compliant Notice of Apr. 20, 2005 for U.S. Appl. No. 10/958,026 (6 pages).

Final Office Action for U.S. Appl. No. 10/958,026 dated Aug. 9, 2005. (6 pages).

Response to Final Office Action dated Aug. 9, 2005 for U.S. Appl. No. 10/958,026 (7 pages).

Advisory Action dated Nov. 2, 2005 for U.S. Appl. No. 10/958,026 (3 pages).

Request for Continued Examination filed in response to Nov. 2, 2005 Advisory Action for U.S. Appl. No. 10/958,026 (5 pages).

Office Action dated Dec. 23, 2005 for U.S. Appl. No. 10/958,026 (8 pages).

Response to Office Action dated Dec. 23, 2005 for U.S. Appl. No. 10/958,026 (7 pages).

Office Action dated Oct. 26, 2006 for U.S. Appl. No. 10/958,026 (7 pages).

Response to Office Action dated Oct. 26, 2006 for U.S. Appl. No. 10/958,026 (8 pages).

Advisory Action dated Jan. 16, 2007 for U.S. Appl. No. 10/958,026 (3 pages).

Request for Continued Examination filed in response to Advisory Action dated Jan. 16, 2007 for U.S. Appl. No. 10/958,026 (4 pages).

Office Action dated Mar. 7, 2007 for U.S. Appl. No. 10/958,026 (10 pages).

Response to Office Action dated Mar. 7, 2007 for U.S. Appl. No. 10/958,026 (17 pages).

Office Action dated Aug. 17, 2007 for U.S. Appl. No. 10/958,026 (8 pages).

RCE & Response to Office Action dated Aug. 17, 2007 for U.S. Appl. No. 10/958,026 (13 pages).

Office Action dated Dec. 21, 2007 for U.S. Appl. No. 10/958,026 (9 pages).

Response to Office Action dated Dec. 21, 2007 for U.S. Appl. No. 10/958,026 (16 pages).

* cited by examiner

SELECTIVELY OPENABLE TISSUE FILTER

BACKGROUND

1. Field of the Invention

The present invention relates generally to tissue receiving systems and more particularly to a tissue filtering and retrieval system that permits selective opening of a tissue filter.

2. Description of the Related Art

Tissue filters, especially for biopsy systems, are used to collect tissue samples taken from a patient during a medical procedure, such as a biopsy. In known systems, the tissue filter is generally placed within a filter canister and then tissue is drawn into the filter by a vacuum source connected to the canister. The tissue is then separated from the fluids that may also be drawn into the canister by the vacuum. The tissue sample may then be retrieved from the filter for analysis. In practice, the tissue filter may be used with a tissue resecting device such as a breast biopsy device. In this case, the tissue is resected from the patient, collected in the filter, and removed from the filter for subsequent pathological evaluation.

Current tissue collection systems are difficult to use and do not provide for easy removal of the resected tissue, or core. Many systems incorporate a cylindrical filter, positioned inside a collection canister that separates the tissues from the fluids and captures the resected tissue. After collection, a retrieval element, or scoop, may be used to "pop out" the resected tissue from the cylindrical filter. In many cases, the tissue core may be difficult to eject using the retrieval element when the filter is full. If the tissue core is successfully ejected, there may still be fine tissue surrounding the filter than was not removed by the retrieval element. Further, when there are fine tissues surrounding the filter, the retrieval element may not be able to lift or scrape the fine tissue from the filter wall in subsequent retrieval efforts. In this case, more samples may need to be taken or the resulting tissues collected may be damaged during retrieval. Additionally, the tissue collection systems using retrieval elements are expensive to manufacture due to the additional parts that must be manufactured and packaged with the filter.

Accordingly, an improved tissue filter is required that facilitates simple, easy, and reliable retrieval of tissue from the filter. The new filter should provide comfortable access to the resected tissue, as well as allow for retrieval of fine tissues that may be stuck directly to the filter wall. Additionally, the improved tissue filter should be less costly to manufacture than current filter designs.

SUMMARY

A tissue filter for medical collection includes a filter body defined by a first member, a second member and filter material secured thereto. The first and second members are selectively engaged with one another to form a collection cavity. The collection cavity has an opening for tissue to flow into the collection cavity. The first member and the second member may be selectively separated to facilitate tissue removal. An additional feature may include clasps engaged with the first and second members to secure the first and second members together.

Further, the first and second members may be connected together by a hinge. Accordingly, the filter body may be selectively opened to expose the interior of the collection cavity and allow for tissue removal.

A tissue filter system is also disclosed that includes a canister and a filter body having a first member, a second member, and filter material. The first and second members may be selectively secured together to define a collection cavity. The filter body is selectively inserted within the canister. A vacuum source is connected to the canister to direct tissue into the collection cavity.

BRIEF DESCRIPTION OF THE DRAWINGS

The features and inventive aspects of the present invention will become more apparent upon reading the following detailed description, claims, and drawings, of which the following is a brief description:

DETAILED DESCRIPTION

Referring now to the drawings, preferred embodiments of the present invention are shown in detail. Although the drawings represent embodiments of the present invention, the drawings are not necessarily to scale and certain features may be exaggerated to better illustrate and explain the present invention. The embodiments set forth herein are not intended to be exhaustive or otherwise limit the invention to the precise forms disclosed in the following detailed description.

Figure 1:
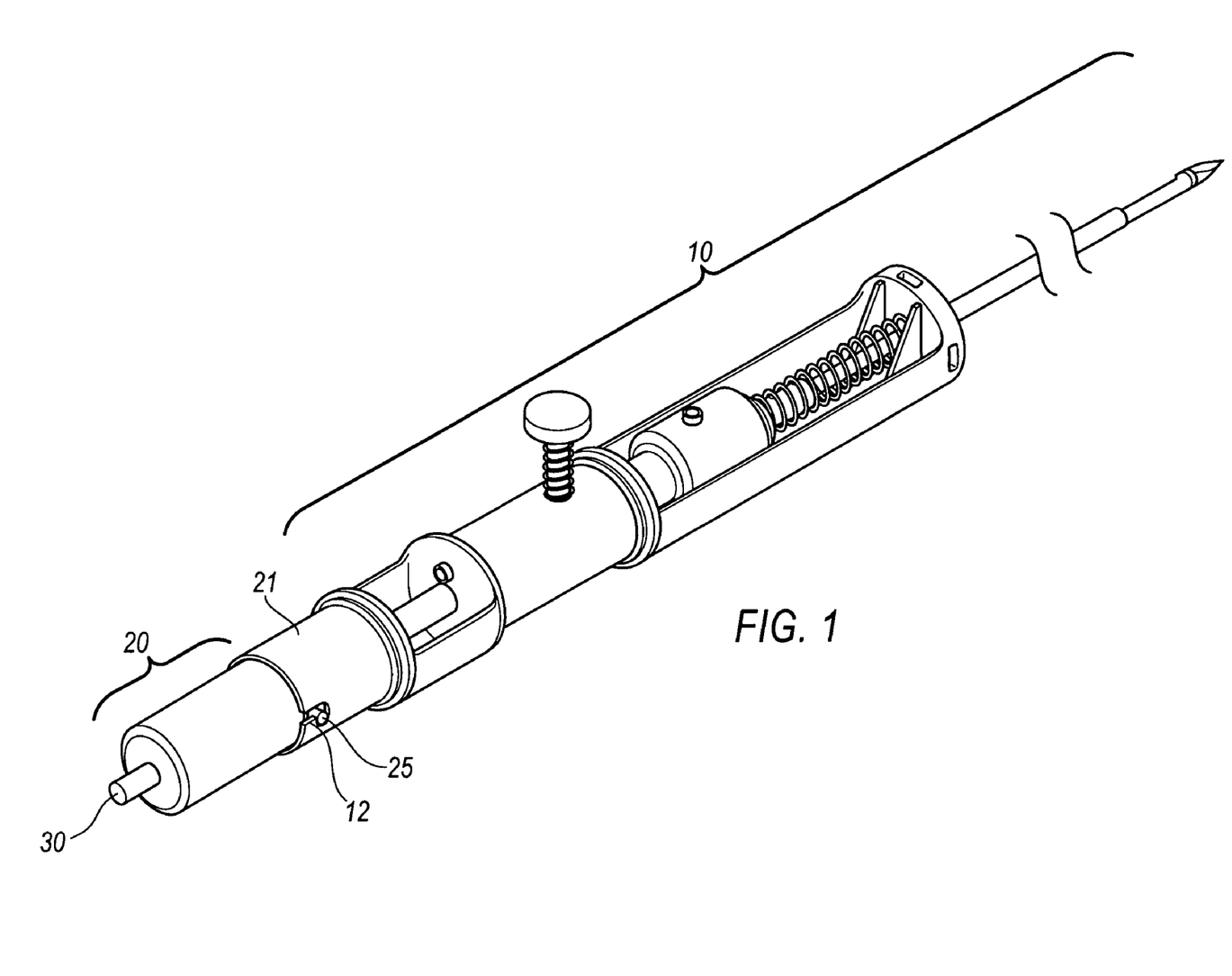
FIG. 1 is a perspective view of a biopsy device having a tissue filter system in accordance with the present invention.

Referring to FIG. 1 is a perspective view of a biopsy device 10 that employs a tissue filter system 20, in accordance with an embodiment of the present invention. Tissue filter system 20 attaches to biopsy device 10 at a receiving hub 21. Receiving hub 21 includes grooves 12 that form a bayonet-type mount for tissue filter system 20. Tissue filter system 20 includes pins 25 (another pin 25, opposite, is not shown) for engaging grooves 12. Grooves 12 and pins 25 work cooperatively to lock tissue filter system 20 into receiving hub 21. Within receiving hub 21, a seal is formed between tissue filter system 20 and biopsy device 10. Tissue filter system 20 further includes a vacuum port 30 for attaching a vacuum source.

In practice, a surgeon uses biopsy device 10 to resect tissue from a patient. The tissue is then drawn through biopsy device 10 by the vacuum source attached to vacuum port 30. Ultimately, the biopsy tissue is drawn into tissue filter system 20 where the tissue is collected for later removal and pathological review. The process and use of tissue filter system 20 with biopsy device 10 is explained in more detail below with respect to FIGS. 2-11.

Figure 2:
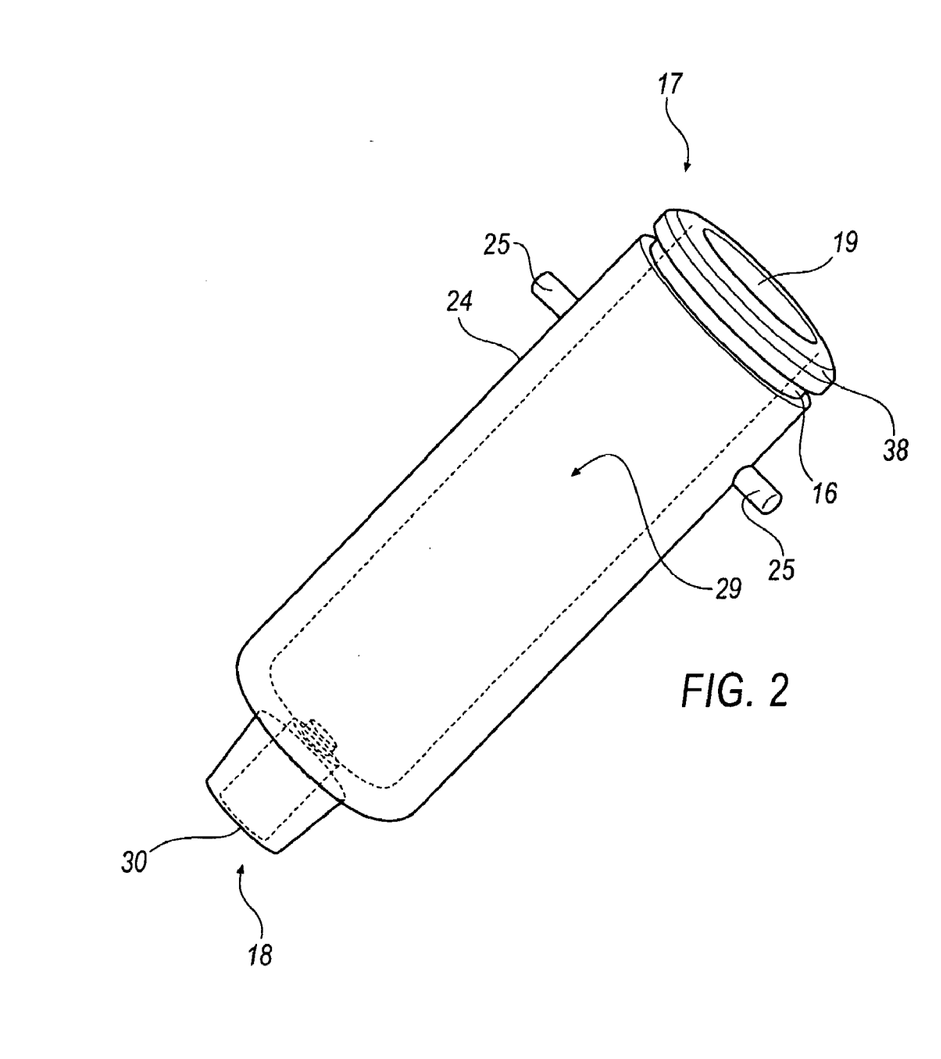
FIG. 2 is a perspective view of a canister for use with the tissue filter system of FIG. 1.
Figure 3:
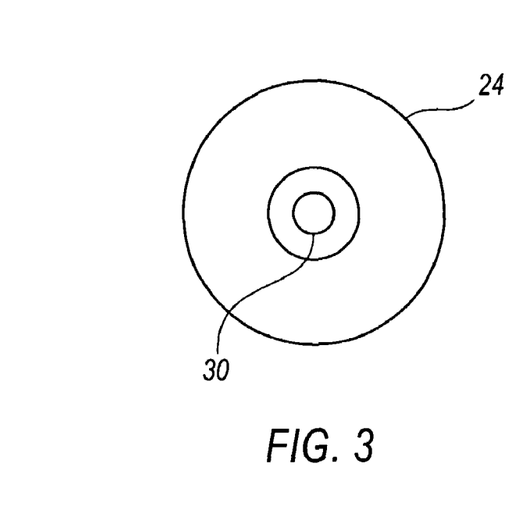
FIG. 3 is a view of a second end of the canister of FIG. 2.
Figures 4, 5:
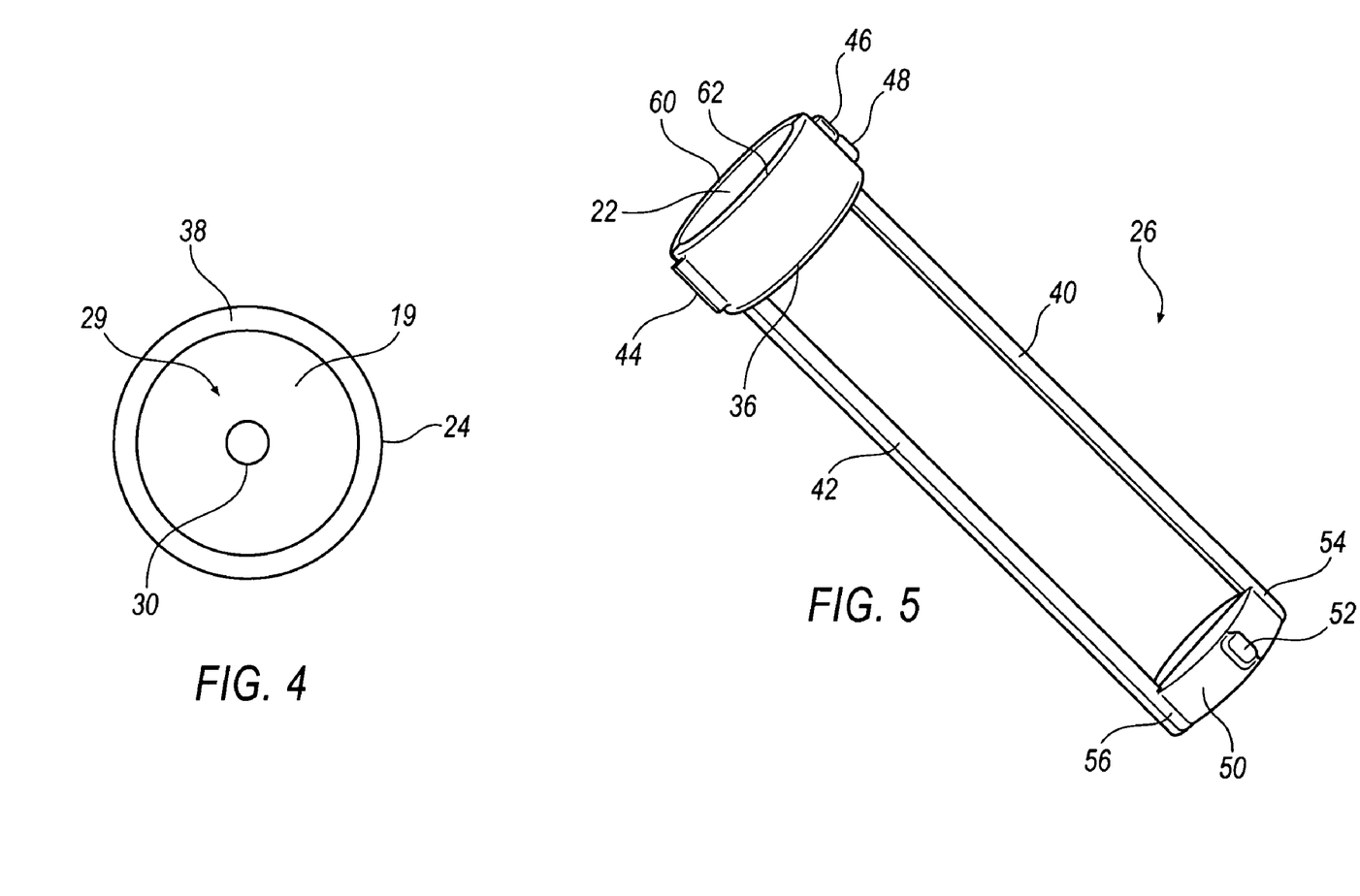
FIG. 4 is a view of a first end of the canister of FIG. 2.
FIG. 5 is a perspective view of a filter body in a closed position for use with the canister of FIG. 2.

FIGS. 2-9 depict specific features of tissue filter system 20. As illustrated in FIGS. 2-4, tissue filter system 20 includes a canister 24. Canister 24 has a generally hollow body including a first end 17 and a second end 18. First end 17 includes an upper rim 38 that is separated from the generally hollow body of canister 24 by an annular groove 16. A filter receiving opening 19 extends through first end 17. Upper rim 38 defines the boundary of filter receiving opening 19.

Second end 18 includes vacuum port 30 for attaching a vacuum source. Vacuum port 30 extends outwardly from second end 18 and is configured to receive a hose (not shown) from a vacuum source to provide vacuum to tissue filter system 20, as will be explained in further detail below. Between first end 17 and second end 18 is a generally hollow collection cavity 29. Filter receiving opening 19 opens to collection cavity 29.

To connect tissue filter system 20 to biopsy device 10, canister 24 includes at least one pin 25 formed on an outside surface of canister 24. Pins 25 are used to engage grooves 12 on biopsy device 10 and lock tissue filter system 20 into sealed engagement with biopsy device 10. (See FIG. 1). As force is applied through pin 25 and groove 12 arrangement, annular groove 16 engages biopsy device 10 within receiving hub 21 (illustrated in FIG. 1). Canister upper rim 38 is pressed against a sealing element within biopsy device 10 to form a seal that withstands the vacuum source applied to vacuum port 30. The seal provides an air-tight or near air-tight seal and thus allows for a vacuum to be drawn from vacuum port 30 through collection cavity 29 such that tissue is drawn through biopsy device 10 and trapped within tissue filter system 20.

In fact, vacuum port 30 is in communication with collection cavity 29 and vacuum is generated by a vacuum source to pull tissue into canister 24. Vacuum port 30 is used to provide an exit route for liquids that are drawn into collection cavity 29 by the vacuum, to be explained in further detail below.

Figure 6:
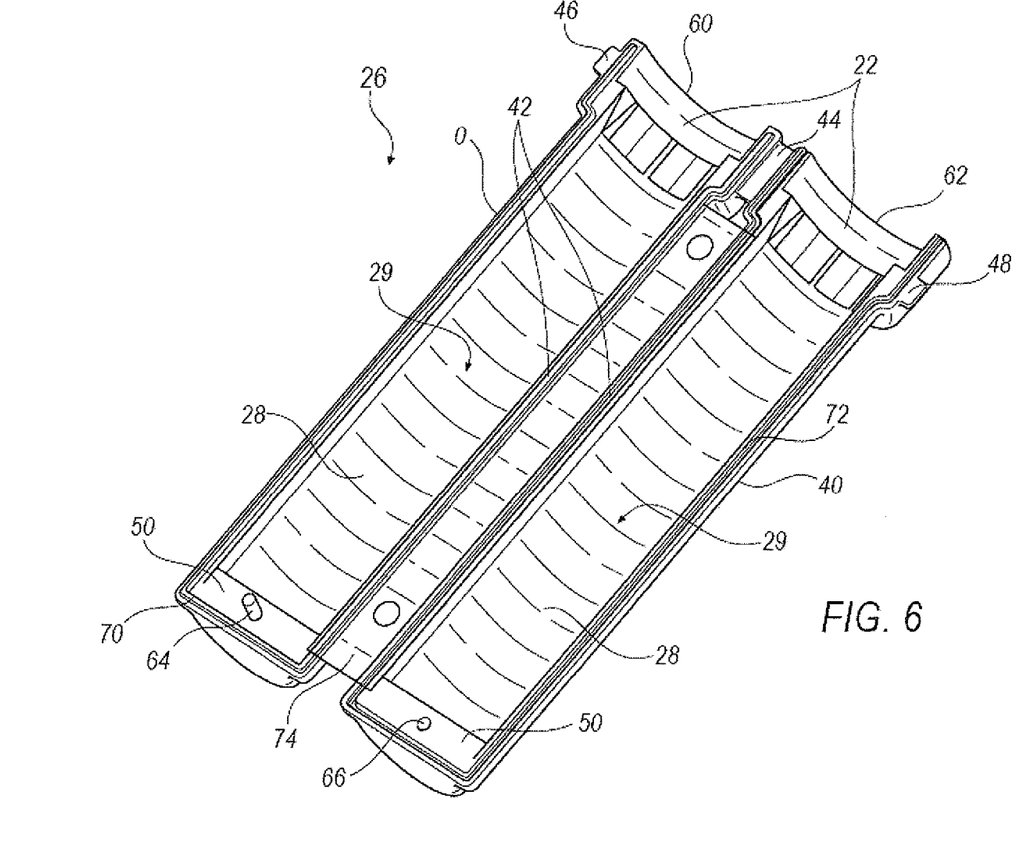
FIG. 6 is a perspective view of the filter body of FIG. 5 in an open position for use with a canister of FIG. 2.

FIGS. 5-6 depict a filter body 26 for use with canister 24. In FIG. 5, filter body 26 is shown in a closed position and without any filter material secured thereto. In FIG. 6, filter body 26 is shown in an open position with filter material 28 secured thereto.

Filter body 26 includes first and second halves 60, 62 each including portions of a lower rim 36 and a base 50. Each half 60,62 has a first pole 40 and a second pole 42 that extend between lower rim 36 and base 50. Poles 40 mate with each other when filter body 26 is in the closed position. Similarly, poles 42 also mate with one another when filter body 26 is in the closed position. Together, poles 40, 42 provide a skeletal framework for filter body 26.

A hinge 44 connects first half 60 to second half 62 and a first clasp 46 and a second clasp 48 cooperate to hold filter body 26 closed. First and second clasps 46, 48 may include tongue and groove elements to facilitate connection to one another.

As shown in FIG. 6, filter body 26 may be selectively opened by disengaging first clasp 46 from second clasp 48. First half 60 and second half 62 remain connected together along hinge 44.

Filter material 28 is secured to filter body 26 and follows the generally circular curvature of an intake 22 and base 50. Filter material 28 may be attached to filter body 26 as a single unitary piece applied to both first half 60 and second half 62 forming a filter hinge 74 between first half 60 and second half 62. In this manner, as shown in FIG. 6, filter hinge 74 becomes a structural element connecting both halves 60, 62 of second pole 42 and assists in aligning the two halves 60, 62 of filter body 26 for closure. Filter hinge 74 also provides support when filter body 26 is in the open position. Alternately, filter material 28 may be applied as multiple separate filter portions applied to first half 60 and second half 62.

Filter material 28 is a hemodialysis-grade mesh filter material designed to capture tissue within collection cavity 29 while allowing fluids to pass therethrough. When filter body 26 is closed, filter material 28 creates a tissue holding boundary within collection cavity 29. As resected tissue is drawn into collection cavity 29 by a vacuum, filter material 28 prevents the tissue from escaping. While filter material 28 does not allow tissue to pass through it, fluids may pass through filter material 28 and are expected to exit tissue filter system 20 through vacuum port 30.

When filter body 26 is closed, first half 60 and second half 62 are aligned near intake 22 by hinge 44. At base 50, a locating key 64 and a locating slot 66 may be used to align first half 60 and second half 62. In one embodiment, locating key 64 is a tab that is received by locating slot 66 to align filter body 26 at base 50. In the closed potion, first half 60 and second half 62 are sealed along the periphery and poles 40 and 42 by a cooperating sealing land 70 and a sealing groove 72 which are mating surfaces. Although the mating connection of sealing land 70 and sealing groove 72 may not form a fluid-tight seal, first half 60 and second half 62 are generally aligned and sealed to the extent that resected tissue may not escape.

Figure 7:
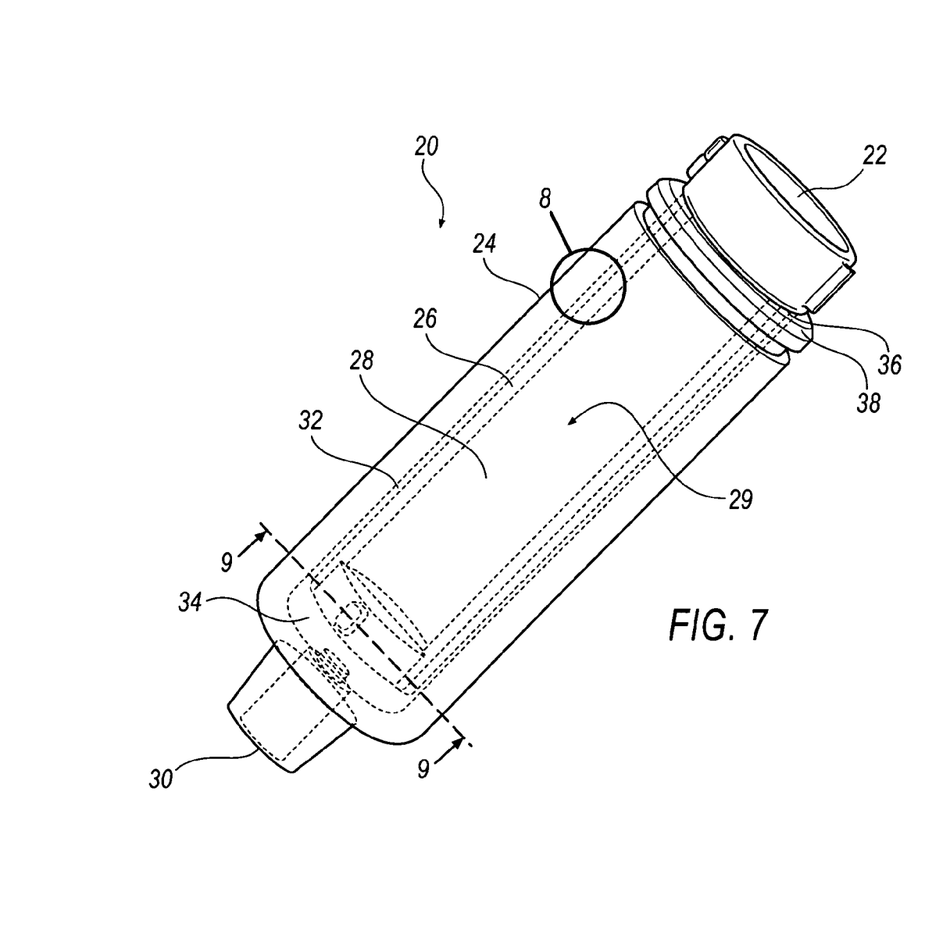
FIG. 7 is a perspective view of the assembled tissue filter system of FIG. 1.

FIG. 7 is a perspective view of an assembled tissue filter system 20. In assembling tissue filter system 20, filter body 26 is inserted into canister 24 through opening 19. Base 50 is inserted first through opening 19 and filter body 26 is pressed into canister 24 until lower rim 36 engages upper rim 38 (illustrated in FIG. 2). Intake lower rim 36 interferes with canister upper rim 38 to limit insertion of filter body 26 within collection cavity 29. Base 50 may include a shape retention tab 52 that spaces base 50 away from canister 24 creating a sidewall gap 32 between filter body 26 and canister 24 (see FIG. 7).

As described above, filter 28 is attached to the interior circumference of intake 22, the inside of first pole 40 and second pole 42, and at base 50. Accordingly, the thickness of first pole 40 and second pole 42 are sized to provide sidewall gap 32 along the length of filter body 26 (illustrated and described in detail below with respect to FIGS. 7-9).

While it is preferred that first clasp 46 and second clasp 48 cooperate to act as a locking mechanism to hold closed a first half 60 and a second half 62 of filter body 26, it should be noted that a locking mechanism is not necessary. In fact, filter body 26 is held closed when placed into canister 24 by frictional contact between first pole 40, second pole 42, shape retention tab 52, and the inner circumference of canister 24.

Sidewall gap 32 (best seen in FIG. 8) and a bottom gap 34 (best seen in FIG. 7) are disposed between the interior surface of canister 24 and the outside surface of filter material 28. Sidewall gap 32 and bottom gap 34 provide a free path for the vacuum to develop along the sides of filter material 28, as well as provide a path for fluids that pass through filter material 28 to exit tissue filter system 20. A vacuum supply is connected to vacuum port 30 creating a low pressure within canister 24 and collection cavity 29. As tissue is resected from the patient, the excised tissue segment enters intake 22 and follows an entry vacuum path $V_1$ through collection cavity 29. Filter material 28 retains the resected tissue within filter body 26 and does not allow the tissue to pass through filter material 28 to sidewall gap 32. However, gasses and/or fluids may pass through filter 28 and flow along an exit path $V_2$ to vacuum port 30.

If a vacuum were not allowed to develop in sidewall gaps 32, tissue filter system 20 would be ineffective at pulling the resected tissues through intake 22 and trapping them inside filter body 26. Similarly, if fluids were not allowed to exit through vacuum port 30, tissue filter system 20 would become full of fluid and a vacuum would not develop within collection cavity 29.

Figure 8:
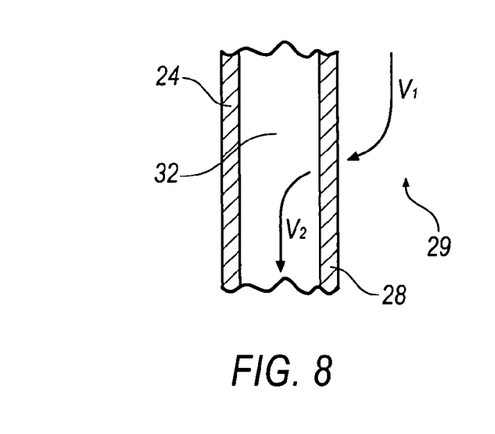
FIG. 8 is a simplified cross-sectional view of the relationship between the filter and the canister in the tissue filter system of FIG. 7.
Figure 9:
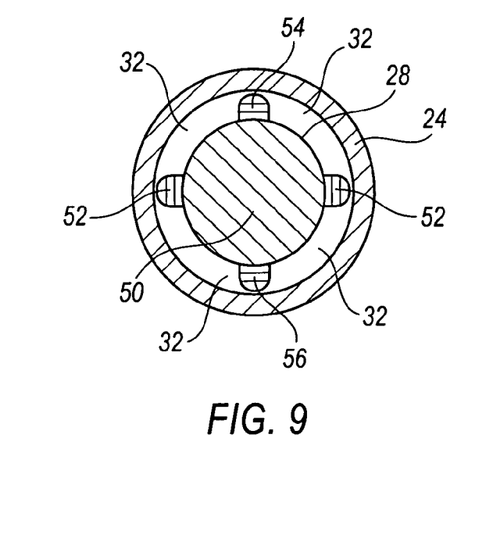
FIG. 9 is a cross-sectional view of a base of the assembled tissue filter system of FIG. 7.

Sidewall gaps 32 are maintained with the cooperation of first pole 40, second pole 42 and shape retention tabs 52 that provide the necessary sidewall gap at base 50. Bottom gap 34 is formed by the void between base 50 and the bottom of canister 24 which is created by the engagement of lower rim 36 of filter body 26 and upper rim 38 of canister 24. Bottom gap 34 is maintained even though vacuum is applied because the interference of intake lower rim 36 and canister upper rim 38 does not allow filter body 26 to move further within canister 24 so as to close bottom gap 34. In summary, canister 24 surrounds base 50, first and second poles 40, 42 and shape retention tabs 52 of filter body 26 (illustrated in FIG. 5). Shape retention tabs 52, and poles 40, 42 create sidewall gaps 32 between base 50 and canister 24. Because filter material 28 follows the general shape of base 50, sidewall gaps 32 are apparent along the length of filter body 26. Thus, as illustrated in FIG. 8, sidewall gap 32 facilitates exit path $V_2$ for fluids to escape from collection cavity 29. Moreover, sidewall gaps 32 function for the development of a vacuum within collection cavity 29 and for the escape of fluids from tissue filter system 20 through vacuum port 30.

Figure 10:
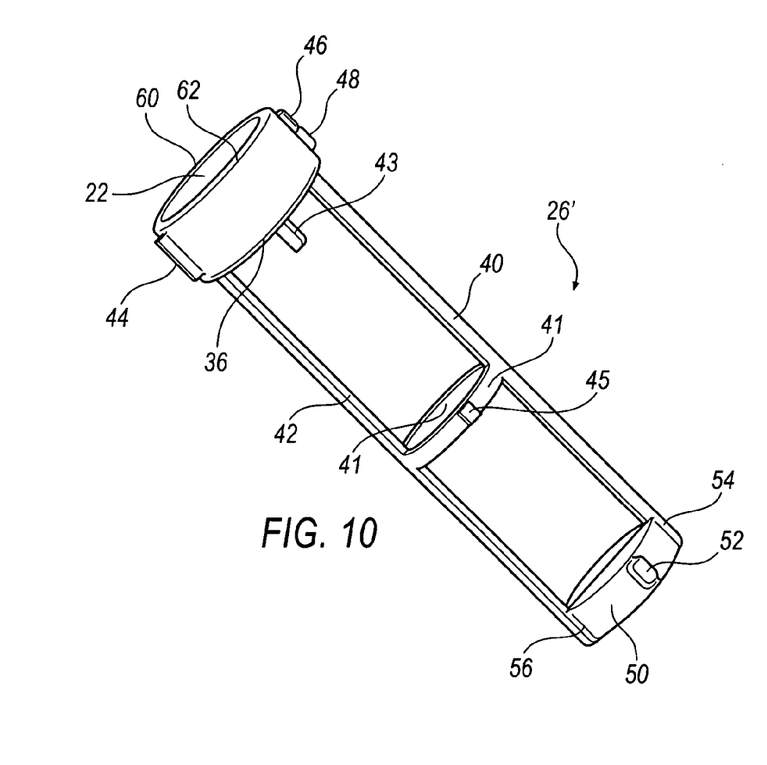
FIG. 10 is a perspective view of an alternative embodiment of a filter body for use with the canisters of FIG. 2 and FIG. 11.
Figure 11:
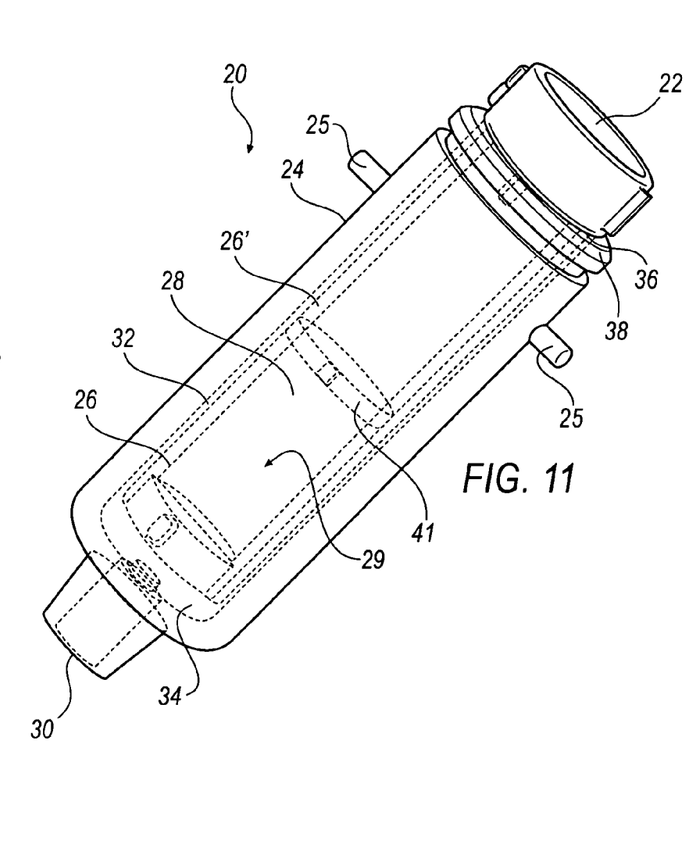
FIG. 11 is a perspective view of an assembled tissue filter system using the tissue filter body of FIG. 10.

FIG. 10 is a perspective view of an alternative embodiment of a filter body 26' in accordance with the present invention. Filter material 28 is not shown for clarity. However, the final assembly of filter body 26' includes filter material 28 attached to filter body 26' as is illustrated in FIG. 6. Filter body 26' includes an intermediate support 41, an upper spacer 43, and an intermediate spacer 45 for use with canister 24 illustrated in FIGS. 2, 11. In this embodiment, first half 60 and second half 62 include intermediate support 41 that extends between first and second poles 40 and 42, approximately mid-way between base 50 and lower rim 36. Intermediate support 41 provides additional support to first pole 40 and second pole 42 while further providing stability for filter material 28 (not shown) under vacuum.

Intermediate spacer 45 also cooperates to maintain sidewall gap 32 (described above in FIGS. 7-9) in the same manner as shape retention tabs 52. Intermediate spacers 45 are positioned on intermediate support 41 and establish sidewall gap 32 along intermediate support 41 so that gap 32 allows vacuum flow along the entire periphery of filter body 26. Without intermediate spacer 45, intermediate support 41 may flex radially outwardly along with filter material 28 and block vacuum generation within collection cavity 29 if filter material 28 is allowed to engage canister 24 under vacuum. Thus, filter material 28 will not collapse sidewall gap 32 under vacuum because intermediate support 41 helps to conform filter material 28 to the appropriate shape and restrain filter 28 from pressing against canister 24. Intermediate spacer 41 also serves as a stop to prevent filter body 26 from opening as tissue segments are received therewithin.

Upper spacer 43 depends downwardly from intake lower rim 36 and provides support for filter material 28 during assembly when filter material 28 is applied to the interior of filter body 26' (as illustrated with filter body 26 in FIG. 4). Further, upper spacer 43 acts as a guide and aligns lower rim 36 of filter body 26' with canister 24 when filter body 26' is inserted into canister 24.

Referring to FIGS. 1-11, the operation of tissue filter system 20 is explained in detail. Tissue filter system 20 is attached to biopsy device 10 creating a seal between tissue filter system 20 and biopsy device 10. (See FIG. 1). A vacuum supply is attached to vacuum port 30 which in turn creates a vacuum in collection cavity 29. As tissue is resected from a patient during a procedure, the vacuum causes the tissue to be drawn through biopsy device 10 and opening intake 22 where the tissue is collected in tissue filter system 20. However, the tissue does not reach vacuum port 30 because filter material 28 stops tissue from escaping collection cavity 29. Thus, the resected tissue is trapped within collection cavity 29 of filter body 26. Fluids and gasses may, however, pass through filter material 28 and exit tissue filter system 20 through vacuum port 30 to be collected in a fluid canister (not shown). Because the resected tissue is of interest in biopsy procedures, tissue filter system 20 is designed to trap the tissue of interest while allowing the fluids to escape through vacuum port 30.

When the surgeon wishes to have access to the collected tissue, the vacuum supply is turned off and tissue filter system 20 is detached from biopsy device 10. Filter body 26 may then be removed from canister 24 to expose filter material 28. In order to have the best access to the resected tissue, filter body 26 is opened to expose the interior of filter 28. As filter body 26 is opened, as illustrated in FIG. 6, the interior of filter body 26 is exposed allowing direct access to the interior collection face of filter 28. To open filter body 26, first clasp 46 and second clasp 48 are pulled apart which in turn opens filter body 26 along hinge 44 and filter hinge 74.

Once filter body 26 is opened, medical personnel may easily remove resected tissue that is trapped within collection cavity 29 of filter body 26. Fine tissue that may be stuck to the surface of filter 28 may also be removed without difficulty since filter 28 is fully exposed. One benefit, among many, of the present invention is the ability to easily retrieve resected tissue or fine tissues from filter body 26 because filter body 26 may be opened. Further, since a scoop mechanism is not required to pull tissue samples from the filter cavity the present invention is easier to use and is less expensive to manufacture than prior art filters.

If further procedures are necessary to collect tissue, filter body 26 may be closed by pinching first clasp 46 and second clasp 48 together. Filter body 26 may then be re-inserted in canister 24 and tissue collection system 20 may be attached to biopsy device 10 for further tissue collection.

The present invention has been particularly shown and described with reference to the foregoing embodiments, which are merely illustrative of the best modes for carrying out the invention. It should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

What is claimed is:

1. A tissue filter assembly comprising:
 a filter body having a first half, a second half, and a hinge;
  the hinge engaging a portion of the first half and a portion of the second half so as to hingedly connect the first and second halves together such that the first and the second halves are selectively movable relative to each other between an open configuration and a closed configuration; the first half and the second half cooperating to provide a tissue structure collection cavity and at least one opening into the tissue structure collection cavity when the first half and the second half are in the closed configuration; and
a filter material engaged with said filter body within the tissue structure collection cavity the filter material and the filter body together creating a tissue collecting boundary when the filter body is in the closed configuration, and wherein the filter material is engaged such that the opening remains uncovered to permit tissue structures to enter the filter body, the filter material only partially filling the tissue collection cavity;
wherein the filter material and the filter body both open together when urged into the open configuration; and where selective access to the tissue structure collection cavity is provided when the first half and the second half are in the open configuration such as to permit removal of tissue structures collected in the tissue collection cavity.

2. The tissue filter assembly of claim 1, further comprising:
clasps associated with the first and second halves, said clasps cooperating to selectively engage the first half with said second half to releasably secure the first half and the second half in the closed configuration.

3. The tissue filter assembly of claim 1, further comprising:
an aperture located on the second half; and
a key disposed upon the first half and cooperatively received by the aperture, whereby said key assists in the engagement of the first half with the second half.

4. The tissue filter assembly of claim 1, wherein said filter material is engaged between said first half and said second half such that said filter material connects said first half and said second half together.

5. The tissue filter assembly of claim 1, further comprising:
a canister substantially surrounding said filter body; whereby said canister includes a generally hollow body, a largely open first end and a largely closed second end, said canister being adapted for selectively engaging a surgical device.

6. The tissue filter assembly of claim 5 wherein said largely closed end includes a vacuum port adapted for securement to a vacuum source.

7. The tissue filter assembly of claim 1, further comprising:
an intermediate support disposed within the tissue structure collection cavity.

8. The tissue filter assembly of claim 7, further comprising:
at least one intermediate spacer disposed on the outside of said intermediate support;
whereby said at least one intermediate spacer provides a gap between said filter and the inside of a canister.

9. The tissue filter assembly of claim 1 wherein the filter material is engaged with the first half and the second half of the filter body whereby said filter body is selectively opened such that access to said interior of the filter material is provided.

* * * * *